US010485560B2

(12) United States Patent
Khalili (10) Patent No.: US 10,485,560 B2
(45) Date of Patent: *Nov. 26, 2019

(54) TOOL FOR CUTTING BONE FOR SURGICAL USE

(71) Applicant: Razor Medical Instruments LLC, Briarcliff Manor, NY (US)

(72) Inventor: Farid Bruce Khalili, Briarcliff Manor, NY (US)

(73) Assignee: RAZOR MEDICAL INSTRUMENTS LLC, Briarcliff Manor, NY (US)

( * ) Notice: Subject to any disclaimer, the term of this patent is extended or adjusted under 35 U.S.C. 154(b) by 292 days.

This patent is subject to a terminal disclaimer.

(21) Appl. No.: 15/621,961

(22) Filed: Jun. 13, 2017

(65) Prior Publication Data
US 2017/0354424 A1    Dec. 14, 2017

Related U.S. Application Data

(60) Provisional application No. 62/350,177, filed on Jun. 14, 2016.

(51) Int. Cl.
*A61B 17/16* (2006.01)
*A61F 2/28* (2006.01)

(52) U.S. Cl.
CPC ...... *A61B 17/1666* (2013.01); *A61B 17/1693* (2013.01); *A61F 2/28* (2013.01); *A61B 17/1635* (2013.01)

(58) Field of Classification Search
CPC ............ A61B 17/1664; A61B 17/1666; A61B 17/1684; A61B 17/1746; A61B 17/1778
See application file for complete search history.

(56) References Cited

U.S. PATENT DOCUMENTS

| 3,633,583 | A | 1/1972 | Fishbein |
| 7,837,686 | B1 * | 11/2010 | Tulkis ................ A61B 17/1666 606/81 |
| 10,016,205 | B2 * | 7/2018 | Sausen ............... A61B 17/1642 |

(Continued)

FOREIGN PATENT DOCUMENTS

DE    102005031402 A1    1/2007

OTHER PUBLICATIONS

International Search Report and Written Opinion from PCT/US2017/037327, dated Sep. 6, 2017, 15 pages.

(Continued)

*Primary Examiner* — Si Ming Ku
(74) *Attorney, Agent, or Firm* — McDermott Will & Emery LLP (57) ABSTRACT

A device is provided, including a cutting rib, the cutting rib including an arcuate portion having an outer sharp edge and a centralizer configured to receive the cutting rib through a radial slot, the radial slot forming a gap with the cutting rib. The arcuate portion of the cutting rib is formed into a profile that follows a surface of the centralizer, the outer sharp edge of the arcuate portion of the cutting rib has a wavy profile that forms a tunnel in the gap between the centralizer and the cutting rib, and the outer sharp edge of the arcuate portion of the cutting rib protrudes outwardly from the surface of the centralizer. A method for using the device to cut bone in a surgical configuration is also provided.

16 Claims, 10 Drawing Sheets

(56) References Cited

U.S. PATENT DOCUMENTS

2004/0049199 A1* 3/2004 Lechot ............... A61B 17/1666
606/80

OTHER PUBLICATIONS

Puma, K., et al., "Impact of Reamer Condition on Acetabular Tissue Preparation", ORS 2017 Annual Meeting Poster No. 0997, 1 page.
Kwong, L., et al., "A quantitative in vitro assessment of fit and screw fixation on the stability of a cementless hemispherical acetabular component", The Journal of Arthroplasty, vol. 9, No. 2, pp. 163-170, 1994.

* cited by examiner

TOOL FOR CUTTING BONE FOR SURGICAL USE

CROSS-REFERENCE TO RELATED APPLICATIONS

The present disclosure is related and claims priority to U.S. Provisional Pat. Appl. No. 62/350,177, entitled TOOL FOR CUTTING BONE FOR USE DURING HIP REPLACEMENT SURGERY, filed on Jun. 14, 2016, the contents of which are hereby incorporated by reference in their entirety, for all purposes.

TECHNICAL FIELD

The present disclosure relates to tools used for cutting bone during joint replacement. One particular application is for a rib assembly to be used for cutting the cavity of the acetabulum when replacing the hip joint by a prosthetic cup.

BACKGROUND

Tools that are used in surgical procedures for cutting bone are often difficult to clean. Prions and soft tissue embedded in the tool from prior use are difficult to remove. Accordingly, to ensure that no cross contamination occurs between uses cutting tools for surgical procedures are typically designed for a single use. Consequently, the cost for such tools can be high. For example, many of acetabular reamers used to cut pelvic bones (e.g., for hip replacement) are made with complex and expensive machinery. Currently available acetabular reamers (e.g., tools for cutting bone conforming to the acetabular socket of the pelvic bone) have complex configurations that require high manufacturing tolerances and still result in significant rejection rates, further increasing manufacturing cost. High costs of manufacture mean high final cost of the tool, which reduces the user's desire to discard such tools after a single use. However, the accuracy of cavities and other cutouts created by used tools is substantially reduced, compared to those created with single use tools.

Additionally, in many instances it has been observed that the preparation time for the cutting process increases dramatically after the first or second use of a currently available acetabular reamer as the reamers get dull. Dull reamers create more heat at bone surface. The temperature at bone surface in these cases has been measured and shown to exceed 56 degrees C. if temperature of bone surface does exceed 56 degrees C. for duration exceeding 10 second thermal osteonecrosis could occur. Moreover, by the sixth time of use, the preparation time may exceed 30 seconds, in some configurations. Thus, a safe lifetime of currently available acetabular reamers is less than six cutting procedures. Additionally to extended preparation times, the size of an acetabulum reamed with a blunt reamer may not accurately represent the desired size. This inaccuracy may then adversely affect implant selection or implantation and complicate post-surgery recovery, reducing the overall effectiveness of the procedure.

SUMMARY

In some embodiments, a device includes a cutting rib, the cutting rib including an arcuate portion having an outer sharp edge and a centralizer configured to receive the cutting rib through a radial slot, the radial slot forming a gap with the cutting rib. The arcuate portion of the cutting rib is formed into a profile that follows a surface of the centralizer, the outer sharp edge of the arcuate portion of the cutting rib has a wavy profile that forms a tunnel in the gap between the centralizer and the cutting rib, and the outer sharp edge of the arcuate portion of the cutting rib protrudes outwardly from the surface of the centralizer.

In some embodiments, a method includes joining a cutting rib and a centralizer to form a cutting assembly, and joining the cutting assembly to a reamer handle. The method also includes providing a rotating motion to the cutting rib assembly through the reamer handle, removing a substrate material by contacting the cutting assembly with a substrate, and adjusting the rotating motion of the cutting rib assembly through the reamer handle according to a substrate condition.

BRIEF DESCRIPTION OF THE DRAWINGS

In the figures, elements having the same or similar reference numeral have the same or similar functionality or configuration, unless expressly stated otherwise.

DETAILED DESCRIPTION

Embodiments disclosed herein include a tool for cutting bone that is simple to clean after use. In some embodiments, disposable tools for cutting bone have a strong, sharp cutting edge that does not fracture when used multiple times and yet is simple to manufacture at low cost. Accordingly, in some embodiments tools as disclosed herein may be disposed after even the first use. Further, tools or reamers for cutting bone as disclosed herein include a selectively disposable cutting rib that provides an accurate and predictable cutout shape (e.g., the acetabular socket in the pelvic area, or hip), thus ensuring predictable and accurate cutting. Further, tools and reamers as disclosed herein can endure high instantaneous torque during reaming and shaping of bone and other substrates.

In some embodiments, tools for cutting bone as disclosed herein include acetabular reamers for hip replacement surgery. Some embodiments of tools for cutting bone include calcar planar ribs to smooth the calcar when implanting the femoral component of a total hip replacement, axial tapered or cylindrical long ribs used in hip or knee replacement used to find and shape the femoral canal and glenoid reamers that are used in shoulder arthroplasty, and others.

During hip replacement surgery, the acetabulum socket in the pelvic bone is prepared for receiving an acetabular cup. Accordingly, the medial floor of the acetabulum socket is identified so that a first acetabular reamer as disclosed herein (of approximately 6 mm or so smaller than a final diameter acetabular reamer) is used to ream medially to the acetabular floor. The initial reamed cavity acts as a centralizer for successive acetabular reamers consistent with the present disclosure. The successive acetabular reamers, of increased dimension, expand the diameter of the acetabular socket. Sequential reamers, as disclosed herein, may be provided in 1 or 2 mm increments in diameter, and are used to further expand the peripheral rim of the socket, while preserving the integrity of the medial and lateral walls.

Reamers may become increasingly blunt with use and should be calibrated, sharpened or replaced. Mid-range reamers (those used most) are most vulnerable to tear and wear from usage. In some embodiments, it is desirable to avoid in vivo diametric deformation of the acetabular shell upon implantation, which may range between 0.0 to 0.57 mm depending on shell thickness and press fit between shell and bone. Such a deformity may affect the integrity of liner/shell locking mechanism. Reuse, high torque and presence of sclerotic bone areas within the acetabular socket, also cause damage to cutting edges of a reamer. Normal repetitive use wears out sharp edges due to fatigue loading. Moreover, the cleaning process used in hospital settings may significantly damage the sharp edges on reamers. Each time after use, reamers are first brushed by hand and soaked into abrasive array of chemicals. They are then placed in a basket and then into an ultrasonic cleaner, so that parts rub against each other, further damaging the sharp edges. Orthopedic surgeons typically operate multiple times in one day. When an orthopedic surgeon uses a dull reamer, he/she is exposed to higher force for a longer period of time to push the reamer into the bone, resisting a higher torque for the reamer to cut similar cavities or sockets. Accordingly, orthopedic surgeons have the highest rate of injury of all surgeons. Shoulders and rotator cuffs in orthopedic surgeons are especially vulnerable regions. Therefore, embodiments as disclosed herein mitigate the above problems by providing selectively replaceable reamers having longer lifetime with sharper cutting edges.

Embodiments as disclosed herein avoid the above problems by providing a selectively disposable cutting rib assembly that a surgeon may easily refurbish during a surgical procedure, discarding at least a portion to rapidly have a new tool ready for use. By providing inter-operative selective disposability, if a surgeon feels that the reamer is dull, cutting ribs in tools as disclosed herein can be instantly swapped with a new one, which could be available in sterile packaging. The cutting ribs can then be returned for disposal or re-sharpening to factory. The cost of refurbishing the tool is thus reduced, the aggregated tool lifetime increased, and the sharpness and precision of the cuts maintained. Further, embodiments as disclosed herein avoid bending fatigue fracture of a cutting edge in the tool by including suitably patterned cutting ribs. Moreover, embodiments as disclosed herein reduce the pressure needed to make contact between the tool and the bone to get the proper fit for implants. This further reduces the need for the surgeon to replace several sets of reamers to complete a single procedure. Embodiments as disclosed herein also reduce maintenance costs of reamers.

Maintenance of reamers has been a costly and resource intensive task for decades. The process removes metal from outer diameter of reamer and requalification of it to previous diametric size is practically impossible. Large orthopedic suppliers have to maintain thousands of reamer sets each with over 20 reamers in it (of varying sizes). Reamer sets are located around the globe and it is highly unlikely to have them inspected after each surgery. Therefore, a surgeon may not be certain that replacement parts holding a sharp edge and meet dimensional accuracy. Some suppliers send their used reamers to a third party for sharpening, at an additional cost.

Figure 1A:
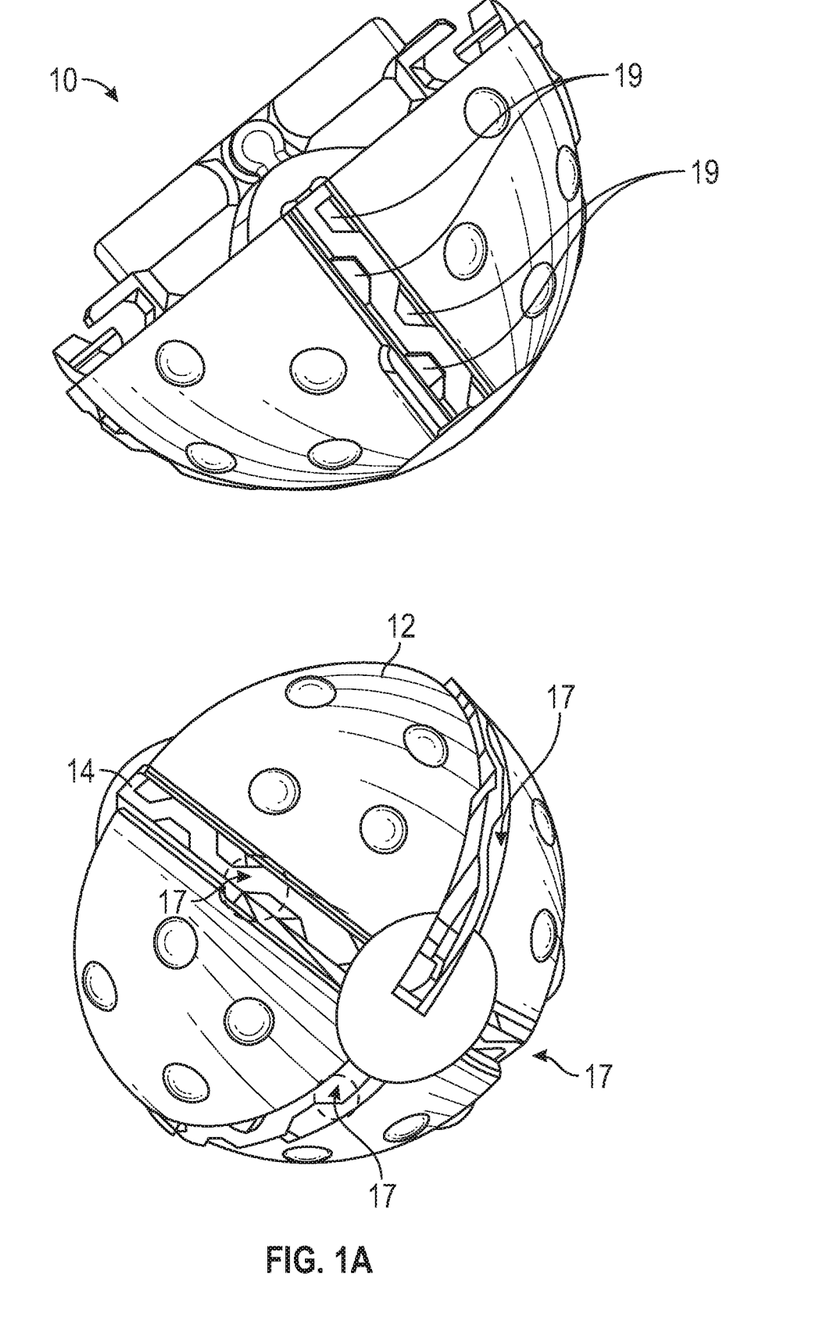
FIG. 1A is a perspective view of a cutting rib assembly, according to some embodiments.

FIG. 1A is a perspective view of a cutting rib assembly 10, according to some embodiments. Cutting rib assembly 10 may include a centralizer 12, and cutting ribs 14. In some embodiments, cutting rib assembly 10 may be selectively disposable. For example, in some embodiments, it may be desirable to selectively remove a portion of cutting rib assembly 10 (e.g., detaching cutting ribs 14 from centralizer 12) to remove bone chips and other residual materials from the assembly for graft purposes, or to replace a portion of cutting rib assembly 10, either intra-operatively, or after a surgical procedure.

In some embodiments, centralizer 12 may have a hemispherical shape to cut into a substrate shaped at least partially in a spherical portion. (e.g., for hip replacement applications). Other geometries may be better suited in different applications. For example, in some embodiments, centralizer 12 may have a radial shape adjusted to better guide cutting ribs 14 in selected areas of the bone socket. Other shapes may be suitable for different applications, such as a more planar shape for "flattening" bone applications, or other shapes more appropriate such as in ankle surgery, and the like. In some embodiments, it is desirable for centralizer 12 and cutting rib assembly 10 to have an axisymmetric shape, where the symmetry axis is the rotation axis of the assembly. More generally, centralizer 12 has a shape configured to form a cutout portion consistent with the acetabular region of a patient's hip or any other anatomic area.

Cutting rib assembly 10 may include multiple unitized cutting ribs 14, which are selectively disposable. Cutting ribs 14 may be detachably assembled to centralizer 12 by fitting within a radial slot 17. In some embodiments, centralizer 12 is also selectively disposable. Centralizer 12 contribute to position cutting ribs 14 within a bone cavity (e.g., the acetabular socket) so that bone is removed to the limit allowed around the diameter of centralizer 12. Centralizer 12 also constrains the range within which cutting ribs 14 can remove or cut bone. Centralizer 12 can be first assembled onto cutting ribs 14. In some embodiments, multiple cutting ribs 14 are assembled symmetrically about an axis of rotation of cutting rib assembly 10, wherein centralizer 12 includes a radial slot 17 for each of cutting ribs 14. Once assembled, the axial motion of centralizer 12 is constrained by cutting ribs 14. Accordingly, an operator (e.g., an orthopedic surgeon) can detach the parts when needed. In some embodiments, centralizer 12 floats radially around and is supported by cutting ribs 14.

In some embodiments, cutting ribs 14 may have a wavy shape, or a shape with alternating forward cutting edges. The wavy shape of cutting ribs 14 further stiffens ribs and provides a plurality of tunnels 19 to guide shaved bone into centralizer 12 for collecting shaved bone. Accordingly, a wavy profile of the blade portion in cutting rib 14 provides strength to an otherwise potentially weak structure, wherein the blade of cutting rib 14 may be as thin as about 1 mm, or even less. In some instances, the wavy shape can include a shape having angulated edges and alternating planar cutting surfaces, and in some instances, the wavy shape can include curvatures. For example, in some embodiments a wavy edge of cutting rib 14 may have an "S" shape, or close to an "S" shape with soft turning of the cutting blade. Further, in some embodiments the wavy edge of cutting rib 14 may have a square profile, with sharp turning edges of the cutting blade. Moreover, in some embodiments the wavy edge of cutting rib 14 may slightly change profile along the distal direction of cutting rib 14. For example, the wavy edge may have a softer, "S"-type configuration in the proximal area and a more square type configuration in the distal area (e.g., close to the tip of centralizer 12). Tunnels 19 allow for collection and passage of bone chips and loose tissue through radial slots 17 into the centralizer and accumulate within the centralizer basket. The bone chips can later be used as auto-graft to fill bone cavities if needed.

Figure 1B:
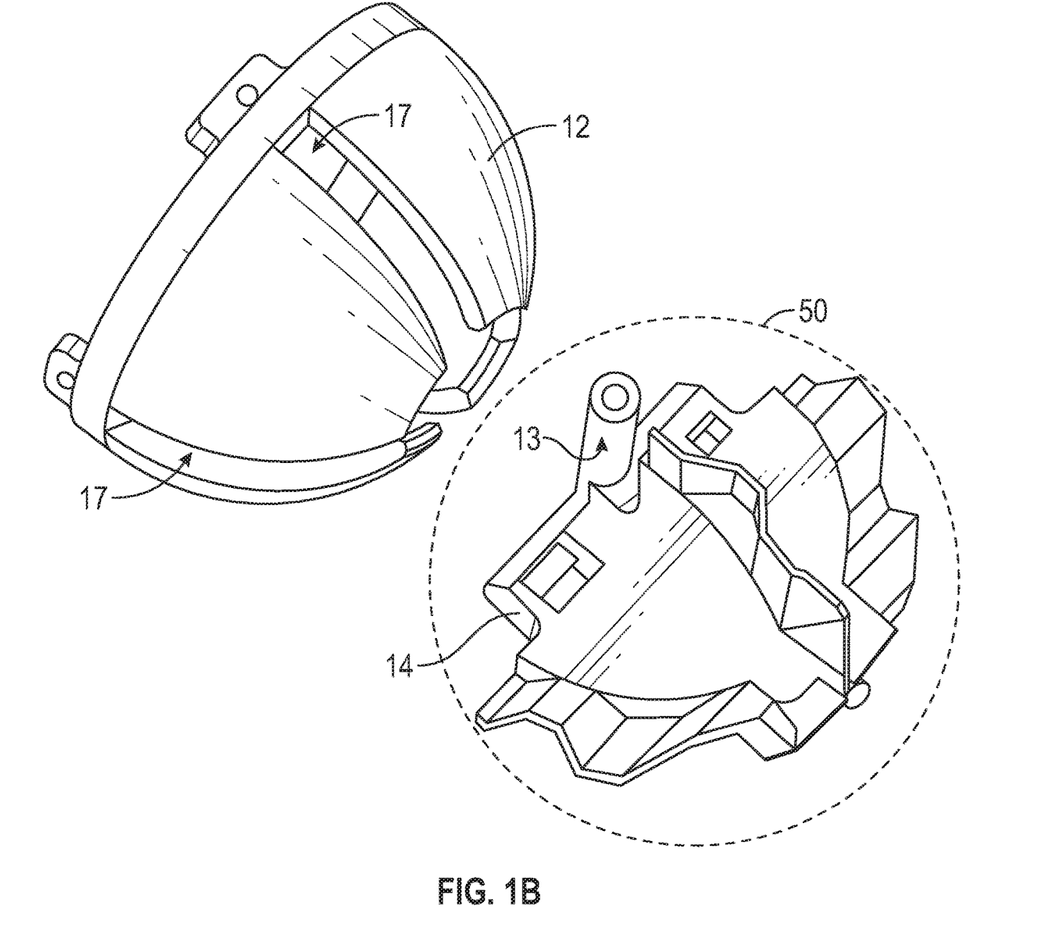
FIG. 1B illustrates an exploded view of a cutting rib and a centralizer, according to some embodiments.

FIG. 1B illustrates an exploded view of a cutting rib 14 and a centralizer 12, according to some embodiments. The proximal part of cutting rib 14 includes a crossbar 13 so that cutting assembly 10 may be driven externally. Crossbar 13 is configured to withstand a high torque from a reamer handle driving a rotation of the cutting rib assembly against the substrate resistance. Embodiments as disclosed herein provide sharp cutting edges in wavy radial ribs that reduce the substrate resistance, thereby relaxing the stress constraint for crossbar 13. Accordingly, crossbars 13 are resistant to breakage from cutting rib assembly 10. More generally, embodiments consistent with the present disclosure may include a geometry at a proximal end of the cutting rib, wherein the geometry is configured to couple with a reamer handle that is configured to provide a rotating motion about a symmetry axis of the centralizer. A geometry as above is understood as a structure in any shape that is consistent with a mechanism to hold the reamer handle.

In some embodiments, centralizer 12 includes a partially hemispherical hollow body of appropriate thickness usually less than 5 mm thick. The hollow body includes a proximal opening and a distal opening with three or more radial slots 17 laterally placed. The cutting rib assembly is made of three (3) or more cutting ribs 14; the edge of each cutting rib 14 is sharpened on the sides that would be cutting bone. The centralizer can be designed to be concentric with blades so that it allows for even removal of bone around it, or, it can be designed not to be centered so that the surgeon can selectively remove more bone from on area versus other. For example, in some patients the acetabular floor of the socket is thin and surgeon may want to not remove bone from the floor but other areas within the socket. Selecting a centralizer 12 that is placed more distal to centerline of blades will shield the floor of the socket and prevent bone removal in that area. After use, the blades can be removed from the centralizer 12 to allow for full access to both parts and facilitate cleaning. They may also be disassembled so as to permit disposal of either part.

In some embodiments, cutting rib assembly 10 is a stiff, unitized structure including a central portion 50 including cutting ribs 14 and crossbar 13. A stiff, unitized structure maintains an accurate relationship between cutting edge and central axis of rotation resulting in an accurate cut. Cutting rib assembly 10 minimizes vibration induced during cutting. The stiffness and strength of central portion 50 relieves centralizer 12 from supporting cutting ribs 14. This reduces substantially a load and vibration transfer from one cutting rib 14 rib to another, thereby enhancing cutting accuracy and a smooth surface finish at the cut surface. Additionally, the configuration using central portion 50 increases manufacturing accuracy for the cutting rib assembly, ensuring concentricity between cutting ribs 14 and centralizer 12. This relaxes constraints in assembly tolerance stack up, substantially reducing manufacturing costs.

Figure 2A:
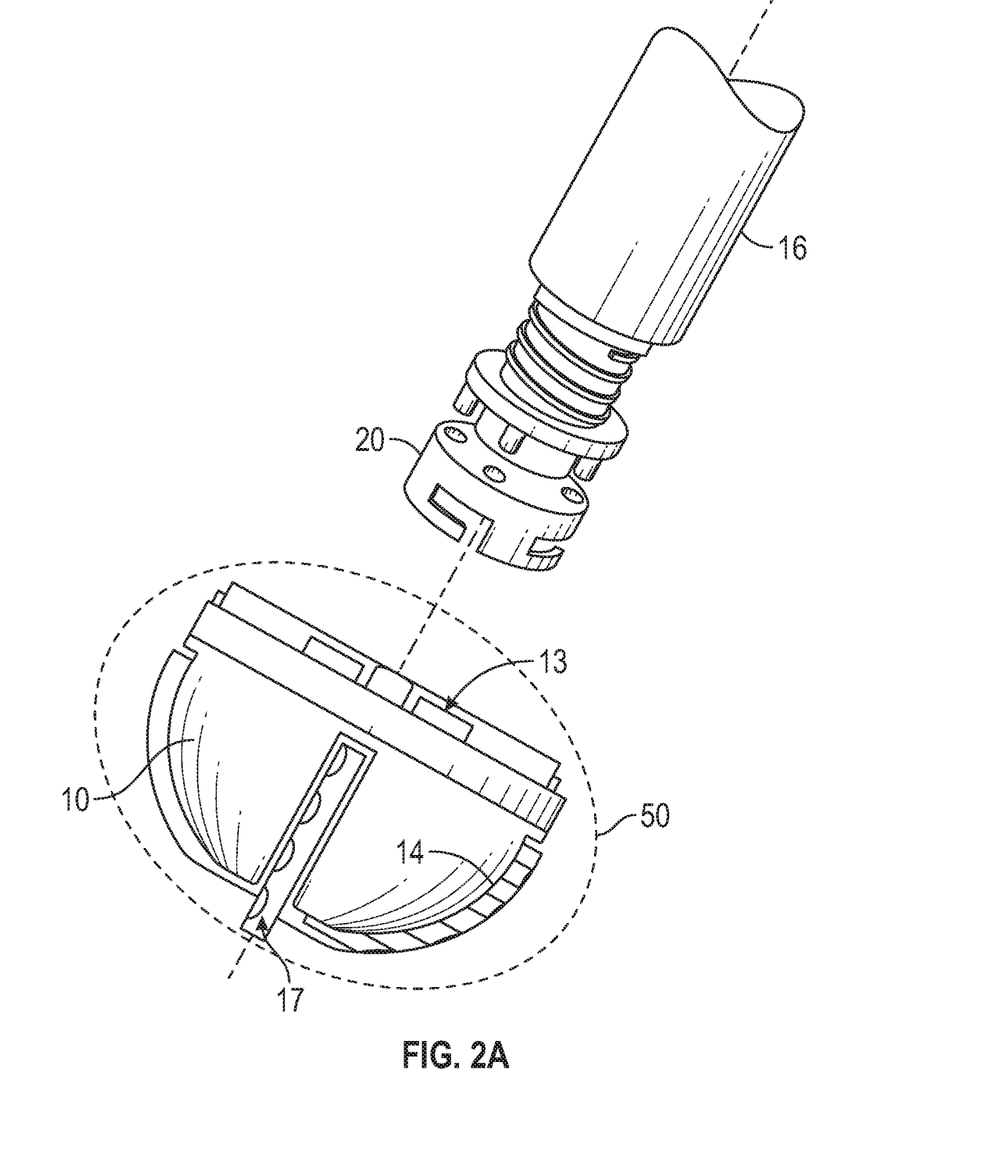
FIG. 2A illustrates an exploded view of the cutting rib assembly and a reamer handle, according to some embodiments.

FIG. 2A illustrates an exploded view of cutting rib assembly 10 and a reamer handle 16, according to some embodiments. Cutting ribs 14 may be directly attached to reamer handle 16 through a coupler 20. In some embodiments, coupler 20 may be a bayonet adaptor. Reamer handle 16 directly delivers torque to cutting ribs 14. The bone cutting edges of each of cutting ribs 14 are sharpened so to cut and shape bone surfaces when rotated and pushed against the bone.

By directly rotating central portion 50 through crossbar 13, cutting rib assembly 10 provides a more accurate hemispherical cut even when crossbars 13 and centralizer 12 are slightly off center. This ensures a tight fit between implant and bone at the acetabular socket, dramatically reducing the failure rate of the procedure. Further, embodiments consistent with the present disclosure reduce any torque transmitted through centralizer 12 to cutting ribs 14, thus reducing chatter, which results in a smooth bone surface finishing. Further, embodiments as disclosed herein minimize the possibility of inducing compounded errors in cutting rib assembly 10. For example, directly coupling reamer handle 16 with crossbar 13 minimizes functional assembly tolerances, as the relative position of centralizer 12 becomes less critical to performance. Also, deflection forces caused by vibration and torque induced through the medium resistance on centralizer 12 are decoupled from cutting ribs 14.

Figure 2B:
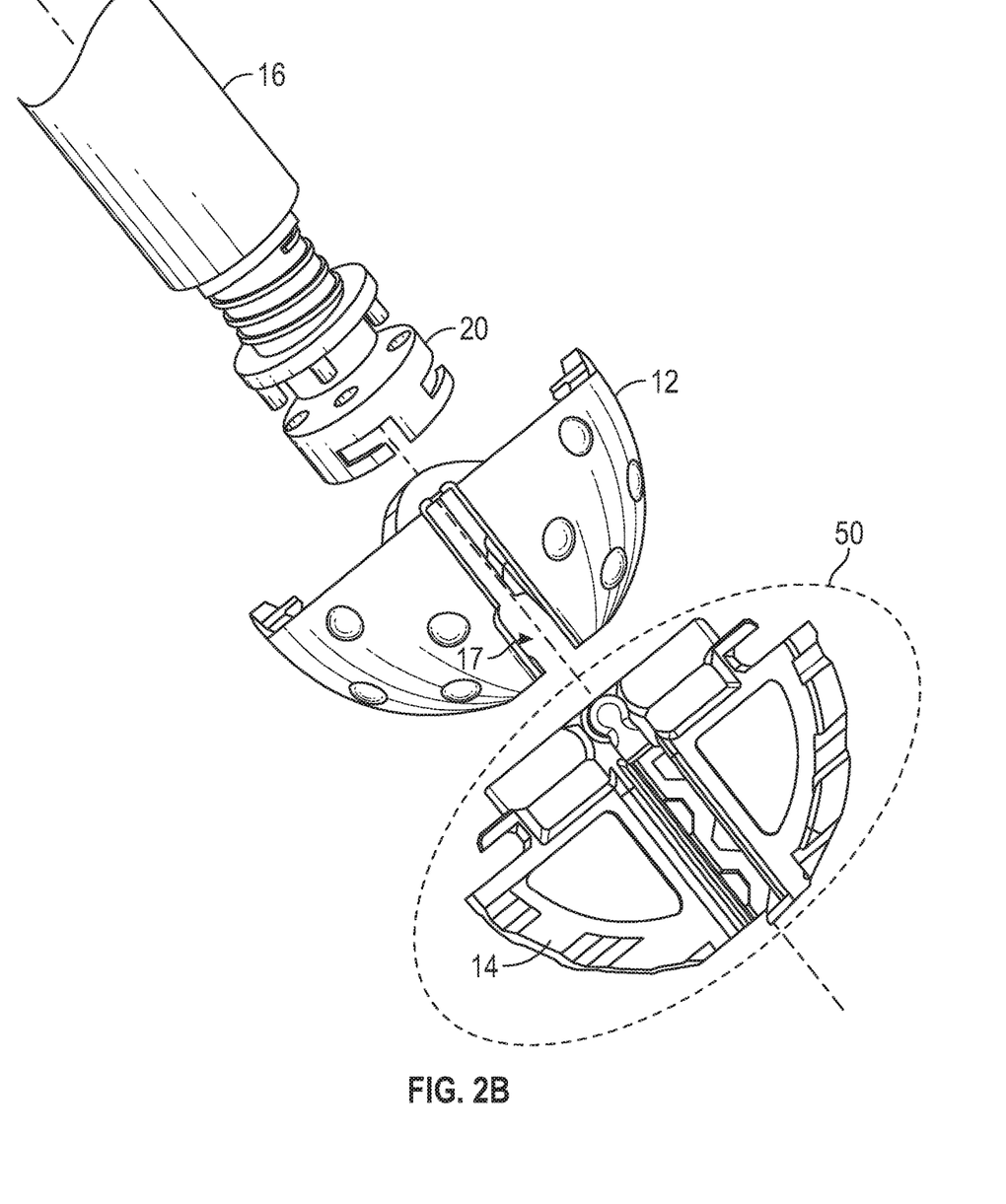
FIG. 2B Shows exploded view of reamer handle, and centralizer, according to some embodiments.

FIG. 2B illustrates an exploded view of rib assembly 10 including cutting rib 14 and centralizer 12 being assembled to reamer handle 16. When reaming the bone; cutting rib 14 may come in contact with harder areas of bone. Such harder areas may include sclerotic bone lesions, which are common in the acetabulum. This will induce a sudden, high amplitude torque applied to the edge of cutting rib 14 which protrudes from an unsupported area of centralizer 12. For example, in some embodiments the blade portion of cutting rib 14 may protrude up to about 1 mm or 1.5 mm out of the surface of centralizer 12. This torque may result in loads that peel cutting rib 14 from cutting rib assembly 10. This torque may also apply a moment arm at the connection area of cutting rib 14 and centralizer 12 resulting in a lift off force of high amplitude. Accordingly, embodiments as disclosed herein reduce the impact of such torque by mechanically de-coupling centralizer 12 from central portion 50.

Additionally, configurations consistent with the present disclosure relax the tolerances for the outer diameter of centralizer 12. Because reamer handle 16 is attached to crossbar 13 in central portion 50, centralizer 12 does not interfere with the rotating motion of cutting rib 14. A more accurate hemispherical cut avoids loss of press fit and fixation between bone and implant, eliminating a potential for early failure because a bone socket with a smaller diameter may have an increased press fit with the implant and may result in formation of a crack around the socket, which is undesirable.

Figure 3:
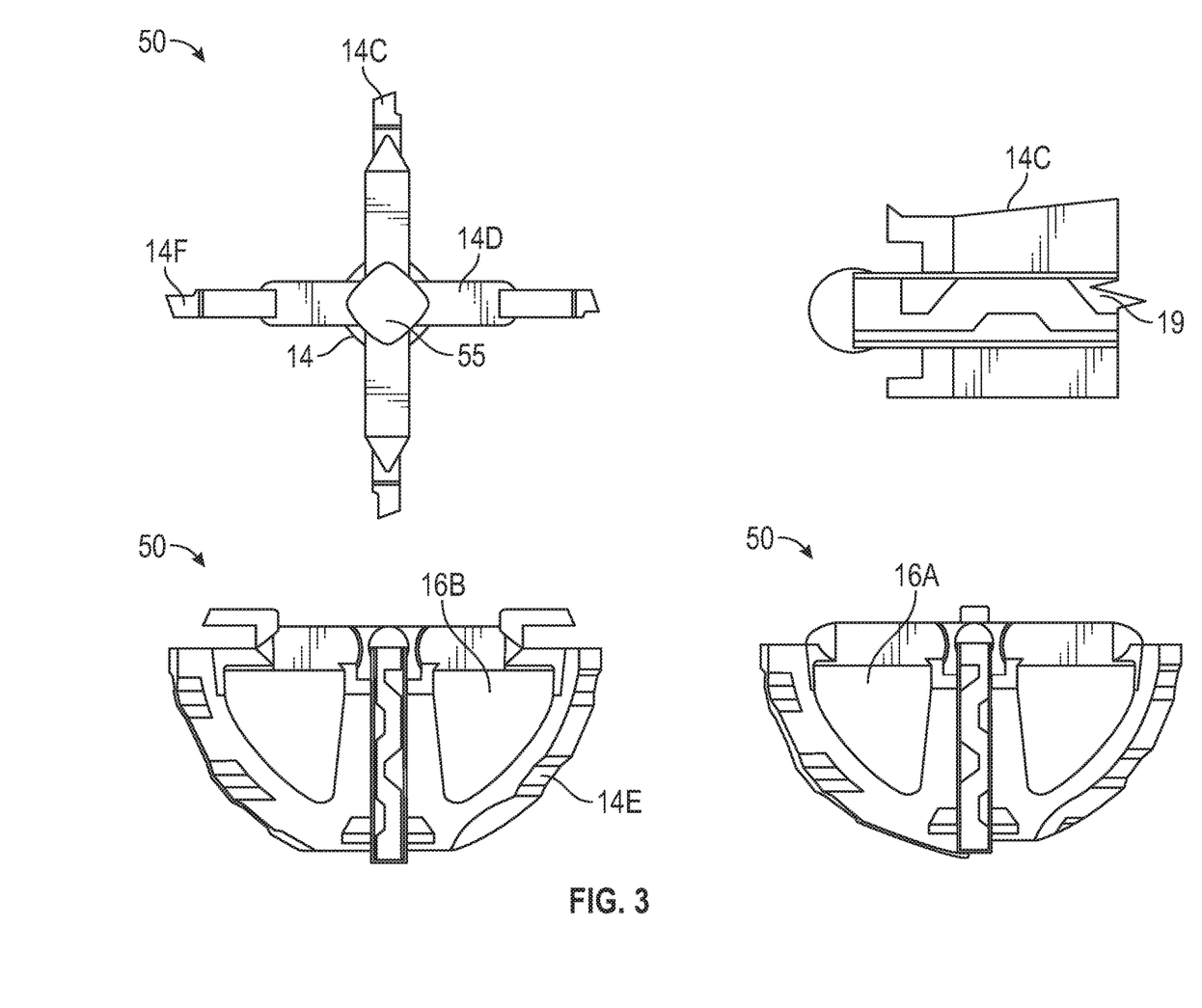
FIG. 3 shows a central portion of a cutting rib assembly, according to some embodiments.

FIG. 3 shows the central portion 50 of cutting rib assembly 10, according to some embodiments. Central portion 50 includes a plurality of cutting ribs 14, having outer sharp edges 14C, 14D, and 14F. Central portion 50 may include windows 16A and 16B that allow attachment of central portion 50 to reamer handle 16. Cutting edges, 14C-F, include a rake angle for a better cutting strength. Tunnels 19 for passage of bone chips are also shown. In some embodiments, central portion 50 also includes a central core 55 formed by interlocking the different cutting ribs 14, which provides a strong support for cutting rib assembly 10.

In some embodiments, central portion 50 is cast from a metal material (e.g., steel, stainless steel, and the like), thereby substantially reducing manufacturing costs as compared to stamping, forging, or other techniques. Central portion 50 distributes the torque between cutting rib assembly 10 and the bone substrate evenly across cutting ribs 14, and avoids mechanical coupling (e.g., through torque) between different cutting ribs 14 (e.g., the torque through central core 55 is negligible, or close to zero, as the radial dimension of central core 55 is highly reduced).

Figure 4:
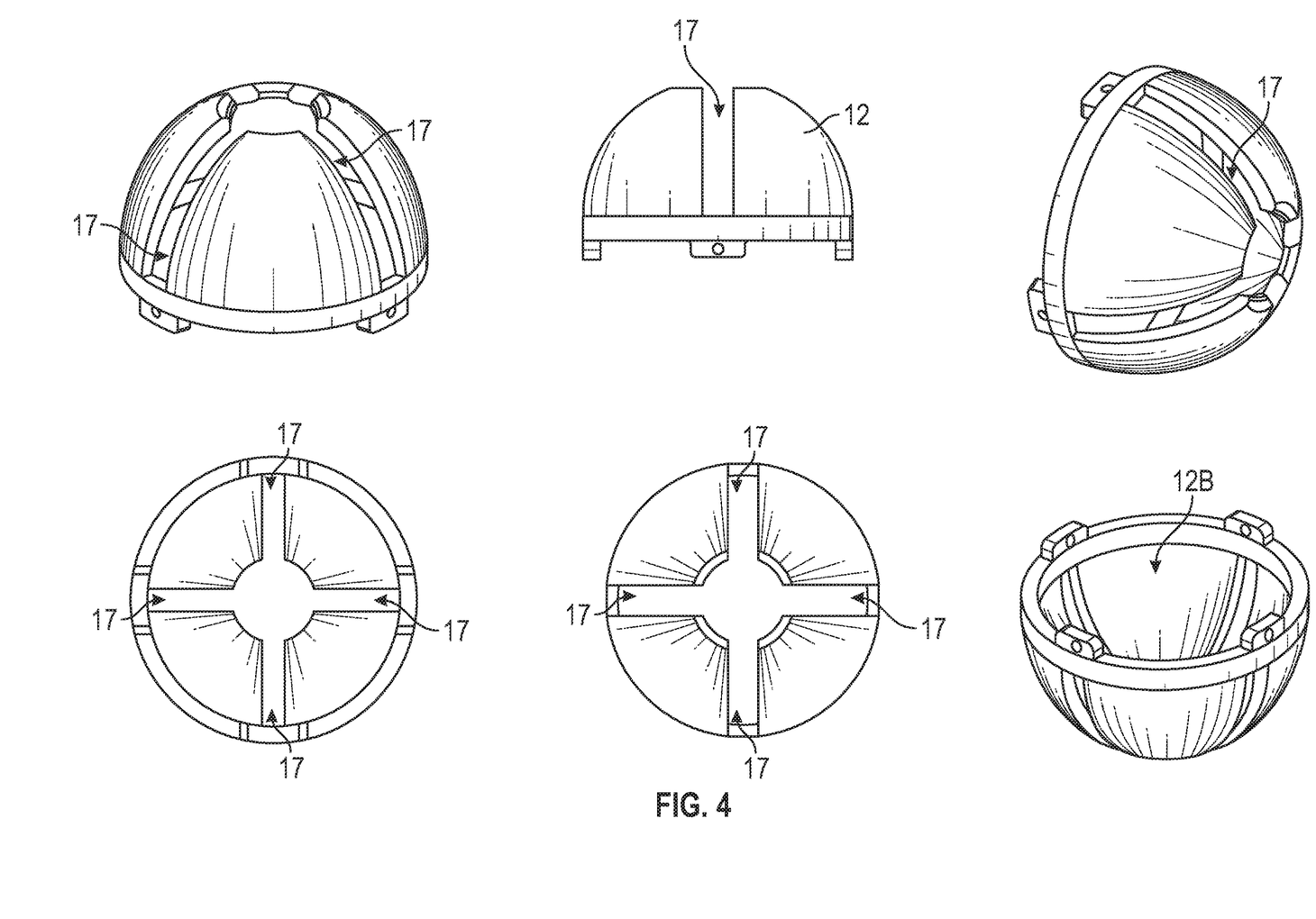
FIG. 4 shows one-piece centralizer, according to some embodiments.

FIG. 4 shows one-piece centralizer 12, according to some embodiments. Radial slots 17 fit cutting ribs 14 that push on one side of centralizer 12 as they rotate. Radial slots 17 provide a passageway for bone chips into the concave portion, 12B, of centralizer 12. The bone chips are collected inside and can later be used to augment bone deficiencies.

Figure 5:
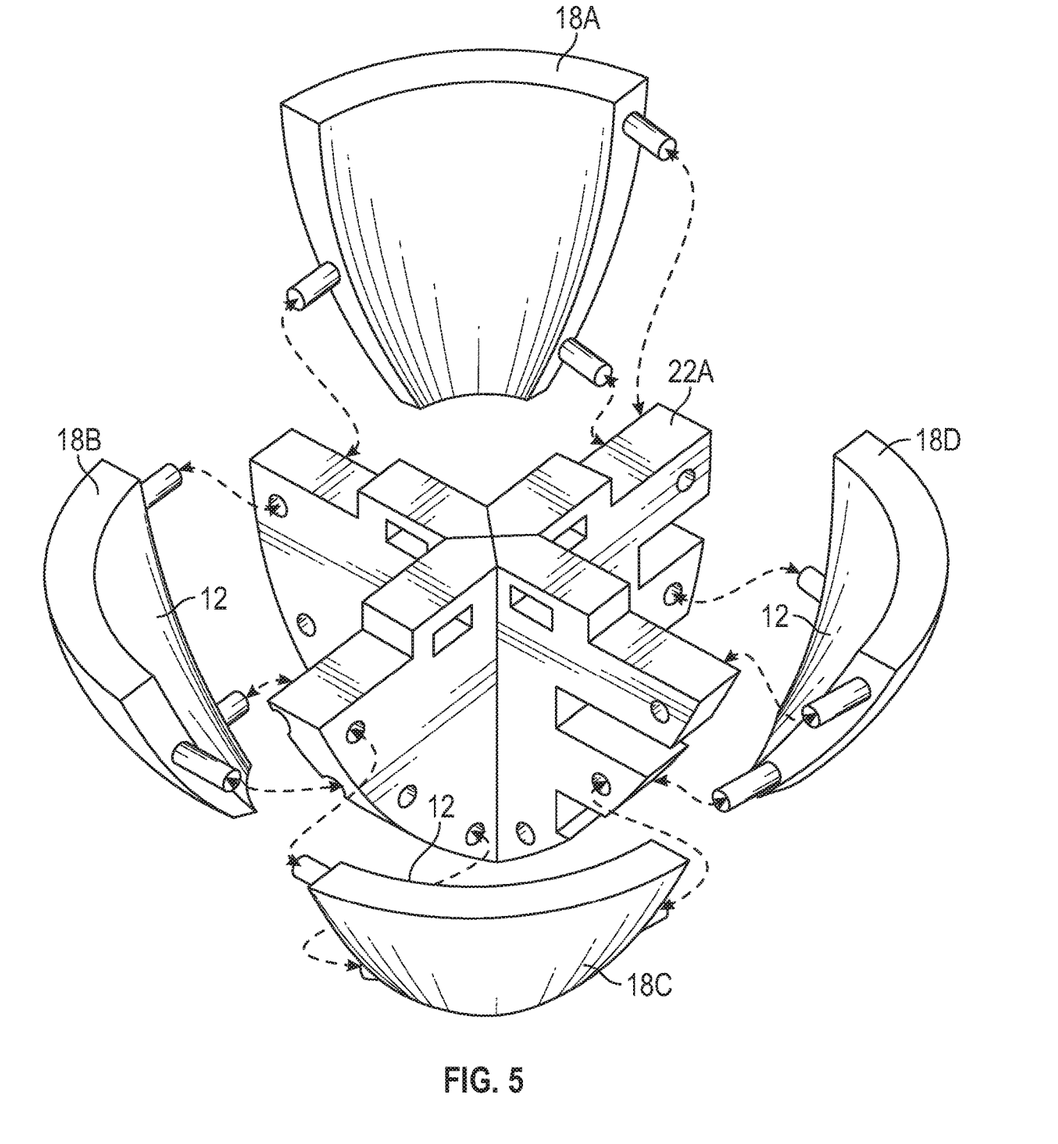
FIG. 5 illustrates view of centralizer and railings, according to some embodiments.

FIG. 5 illustrates a view of centralizer 12 and railing 22A, according to some embodiments. In some embodiments, centralizer 12 includes portions 18A, 18B, 18C, and 18D (hereinafter, collectively referred to as "portions 18"). Accordingly, portions 18 can be snapped together with railing 22A to form a cutting rib assembly. Centralizer 12 is therefore easy to replace after use of cutting assembly 10, or even intra-surgically, as the surgeon determines that a certain amount of bone tissue has already accumulated in concave portion 12B. In some embodiments, portions 18, which are detachable, may be simply cleaned of bone tissue and then snapped back in place for continued use in centralizer 12. In some embodiments, portions 18 may be replaced with new portions 18, for continued use intra-surgically, or in a future surgical procedure. Further, according to some embodiments, portions 18 may be formed of a soft and light material, such as plastic.

Figure 6A:
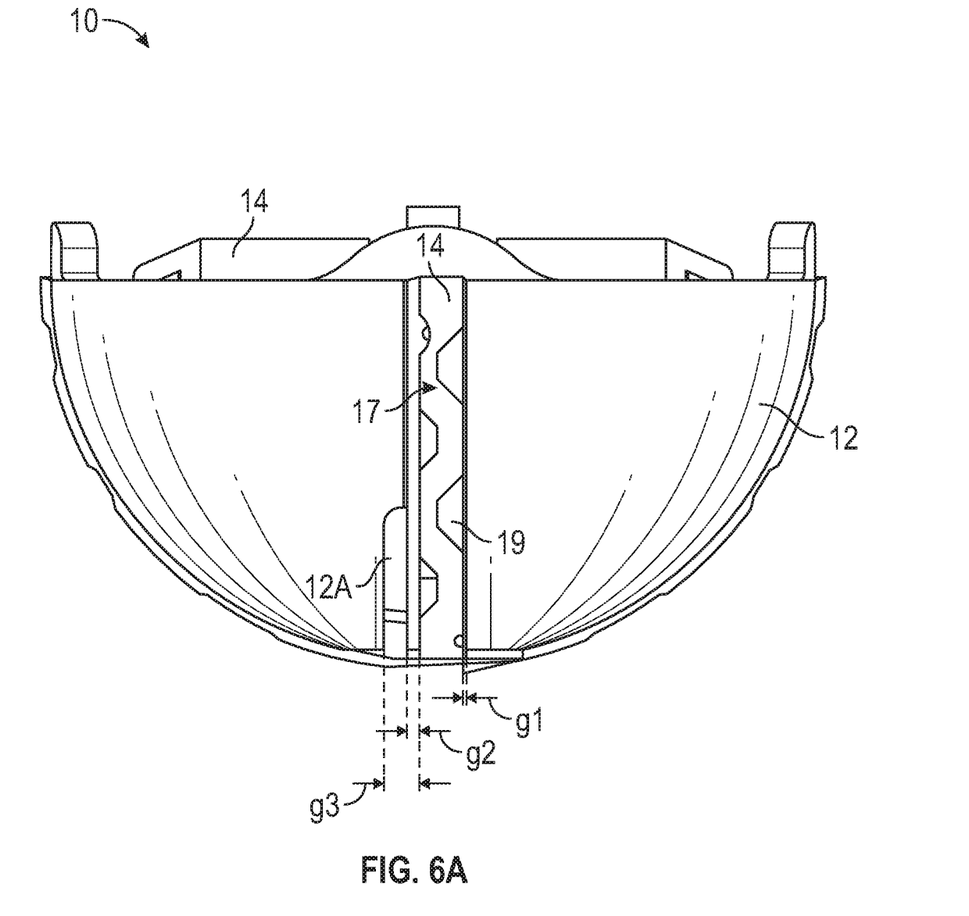
FIG. 6A illustrates clearance between railing and ribs, according to some embodiments.

FIG. 6A illustrates a clearance 12A between radial slot 17 in centralizer 12, and a cutting rib 14 in cutting rib assembly 10, according to some embodiments. Clearance 12A provides ample radial clearance around cutting rib 14 to assure load and vibration are not carried from one cutting rib onto another. Thus, the interplay between radial slot 17 and clearance 12A substantially reduces chatter during use of the device cutting rib assembly 10. Specifically, the increased dimension of the gap in clearance 12A between centralizer 12 and cutting ribs 14 extending along a distal portion of the blade length enables residual bone material to be efficiently removed from the contact area of the blade through tunnels 19. For example, a gap, $g_1$, between radial slot 17 and cutting rib 14 may be about 0.4 mm in a proximal portion of the blade length (upper part of FIG. 6A, as indicated). And a gap, $g_2$, between the opposite side of radial slot 17 and cutting blade 14 may be slightly larger than $g_1$, for example and without limitation, about 1 mm or more. Further, a gap, $g_3$, between centralizer 12 and cutting rib 14 including clearance 12A may be increased to over 2 mm, or about 2.2 mm, or even more, according to some embodiments.

In some embodiments, the slight asymmetry between the left side of radial slot 17 and the right side of radial slot 17 is selected so that increased gap $g_2$ and clearance 12A forming further increased gap, $g_3$, occur on a side facing the direction of rotation of cutting rib assembly 10 (e.g., the left side in FIG. 6A, or the "front" of cutting rib 14). Accordingly, the tissue that is being removed by cutting rib 14 has a space to accumulate under tunnel 19 and be channelized to interior side 12B of centralizer 12. Further, as shown in FIG. 6A, the increased gap, $g_2$, and further increased gap $g_3$ are accrued along the distal direction of centralizer 12. This gradual increase of the gap between radial slot 17 and cutting rib 14 along the distal direction efficiently promotes the residual bone tissue to be transferred to interior side 12B through tunnel 19. For example, in some embodiments it is expected that the speed of cutting rib 14 relative to the bone tissue be larger in the proximal region (larger radius of travel) of centralizer 12 than in the distal region (shorter radius of travel).

More generally, in some embodiments radial slot 17 forms a first gap, $g_1$, with cutting rib 14 at a proximal region on a back end of cutting rib relative to a cutting direction, and a second and a third gaps ($g_2$ and $g_3$) with cutting rib 14 at a distal region on a front end of cutting rib 14 relative to the cutting direction. In some embodiments, the first gap, $g_1$, is different in size than the second gap, $g_2$, and the second gap, $g_2$, is smaller than the third gap, $g_3$. Further, in some embodiments the third gap is approximately two millimeters or more.

Further, as disclosed herein gaps $g_1$, $g_2$, and $g_3$ enable a mechanical decoupling between cutting ribs 14 and centralizer 12, which further enables the low or negligible torque transfer between different cutting ribs 14, thereby substantially reducing chatter and vibration of cutting rib assembly 10 as the bone tissue is being reamed.

Embodiments consistent with the present disclosure relax the manufacturing constraints on centralizer 12 and cutting ribs 14. For example, a thickness of cutting rib 14 and a width of radial slot 17 may have a larger tolerance because of the lack of mechanical coupling between cutting rib 14 and centralizer 12. Additionally, the relative positioning of radial slots 17 may sustain larger tolerances. Accordingly, the cost of manufacturing is reduced. In some embodiments, press-fitting cutting ribs 14 into centralizer 12 may not be necessary. This may avoid distorting the shape of centralizer 12.

Figure 6B:
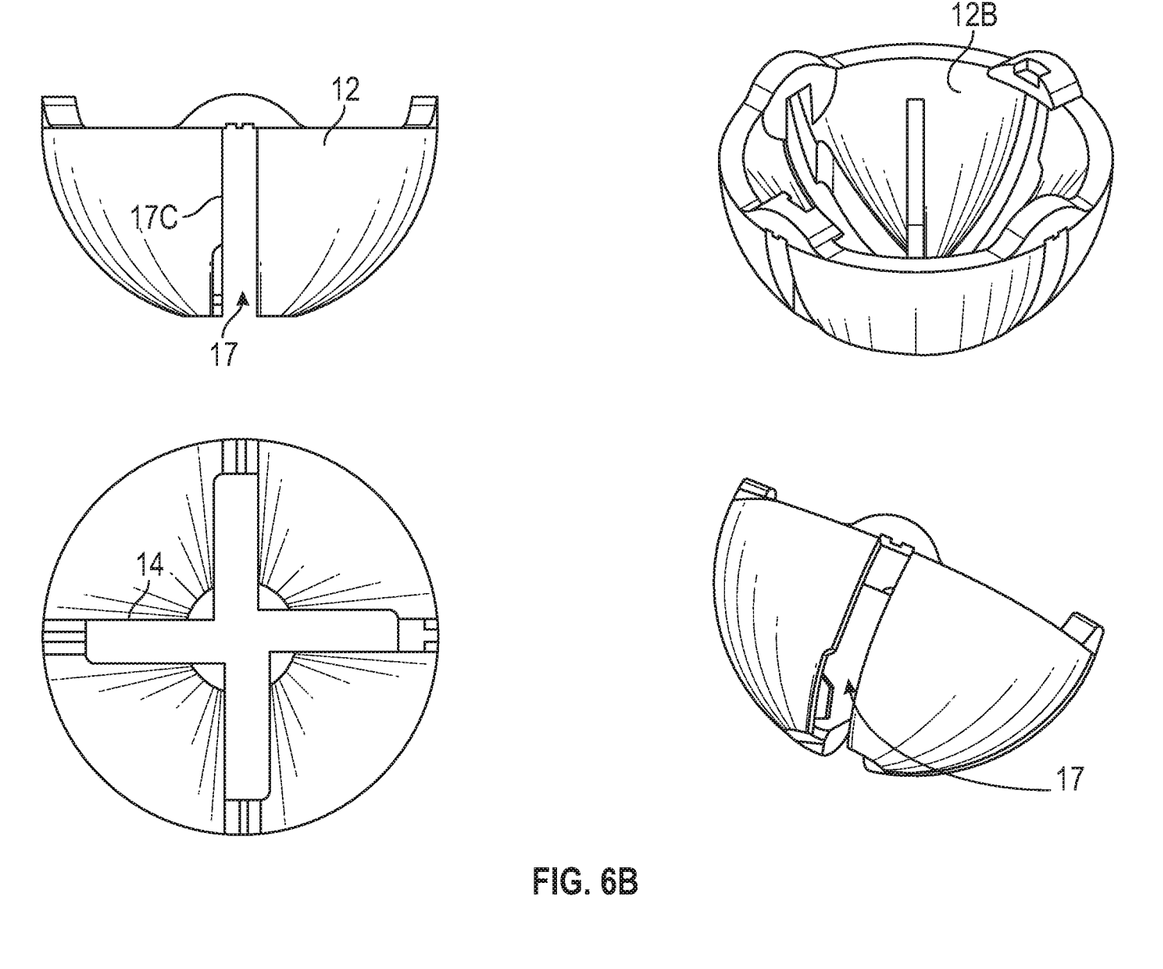
FIG. 6B illustrates a partially hemispherical centralizer with a proximal and distal opening, according to some embodiments.

FIG. 6B shows partially hemispherical centralizer 12 with a proximal and a distal opening. Centralizer 12 includes radial slots 17 to fit cutting ribs 14. As cutting rib 14 rotates, it pushes only one of the sides 17C of radial slot 17 to turn the centralizer 12. Radial slot 17 provides a passageway, a collection passageway, or a collection chamber for bone chips and cartilage to be collected into the concave shape of the centralizer 12B. The bone chips inside can be collected and later used to augment bone deficiencies (e.g., via grafting).

Figure 7:
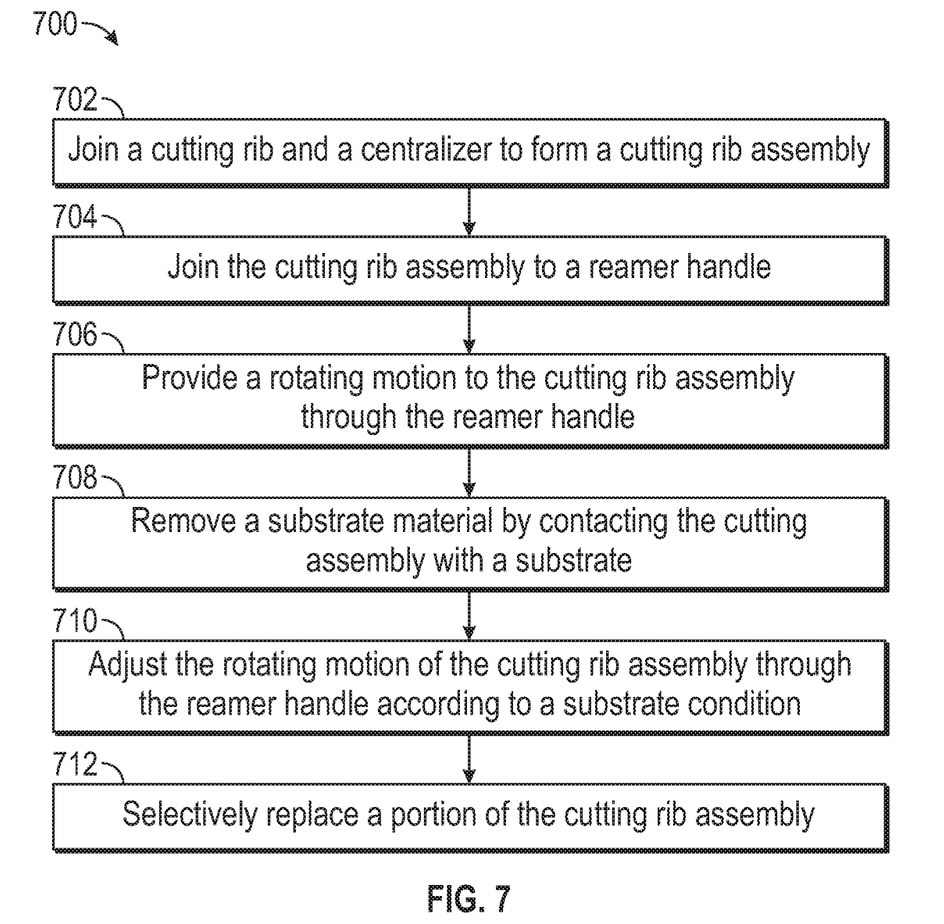
FIG. 7 illustrates a flow chart including steps in a method for removing a substrate material using a tool, according to some embodiments.

FIG. 7 illustrates a flow chart including steps in a method 700 for removing a substrate material using a tool, according to some embodiments. In some embodiments, steps in method 700 may be used in conjunction with a surgical tool for cutting bone. The surgical tool may include a cutting rib assembly having cutting ribs, a centralizer, and a distal plug (e.g., cutting rib assembly 10, cutting ribs 14, and distal plug 15). Further, in some embodiments the surgical tool may include a reamer handle (e.g., reamer handle 16) to provide a rotating motion to the cutting rib assembly, the reamer handle may be coupled with the cutting rib assembly through a crossbar (e.g., crossbar 13).

Further according to some embodiments, methods consistent with method 700 may include at least one, but not all, of the steps illustrated in FIG. 7. Moreover, in some embodiments, a method as disclosed herein may include steps in method 700 performed in a different sequence than that illustrated in FIG. 7. For example, in some embodiments, at least two or more of the steps in method 700 may be performed overlapping in time, or even simultaneously, or quasi-simultaneously.

Step 702 includes joining the cutting rib and the centralizer to form the cutting rib assembly. In some embodiments, step 702 may include adjusting a crossbar in the cutting rib to protrude beyond the centralizer and form a proximal end of the cutting rib assembly.

Step 704 includes joining the cutting rib assembly to the reamer handle. In some embodiments, step 704 may include joining a distal end of the reamer handle with a proximal end of the cutting rib assembly. Accordingly, in some embodiments the distal end of the reamer handle is configured to firmly grab the crossbar in the cutting rib.

Step 706 includes providing a rotating motion to the cutting rib assembly through the reamer handle.

To ease cutting the bone, surgeons use powered reamer drivers. They can spin as fast as 750 revolutions per minute (RPM). In some embodiments, a preferred rotational speed of reamers and tools as disclosed herein may be 350 RPM, or even lower than 350 RPM. More generally, surgeons may use reamers and tools as disclosed herein at speeds between about 350 RPM and about 750 RPM. At such speeds, chips have to be effectively removed from the cutting surface of the rib and the cavity otherwise they will be clogging the cutting edge and hinder cutting and advancement of the reamer. If the slot in the centralizer is in close proximity or attached to the cutting rib, it would then hinder the passage of bone chips into the centralizer. Slots have to be distanced radially from the cutting edge sufficiently to allow the passage of soft tissue, cartilage and bone chips.

Step 708 includes removing a substrate material by contacting the cutting assembly with a substrate. In some embodiments, step 708 includes bringing the cutting rib assembly into contact with a substrate to remove substrate material.

Step 710 includes adjusting the rotating motion of the cutting rib assembly through the reamer handle according to a substrate condition. In some embodiments step 710 may include measuring the temperature of the substrate.

When reaming bone, friction between the cutter edge and bone generates heat. It is generally accepted that the critical level at which thermal necrosis appears in bone is when the bone is exposed to a temperature of around 56° C., over a time span exceeding 10 seconds. At this temperature the denaturation point of alkaline phosphatase is reached, which means that the change in properties are directly attributed to the reorientation of collagen molecules and hydroxyapatite. In some embodiments, reamers under constant load and RPM generate more heat than new reamers and temperatures exceeding 56° C. after the 6 use.

Healing, following bone surgery, may be delayed or even prevented if the bone cells are injured by thermal necrosis resulting from frictional heat generated during surgical preparation.

Accordingly, in some embodiments, step 710 may include reducing a rotating speed of the cutting rib assembly when the temperature of the substrate rises above a desirable level. Likewise, in some embodiments step 710 may include increasing the rotating speed of the cutting rib assembly when a harder portion of the substrate is reached. In some embodiments, step 710 includes adjusting a cutting angle of the cutting rib assembly relative to the substrate (e.g., an axis normal to a plane tangential to the substrate's surface).

Step 712 includes selectively replacing a portion of the cutting rib assembly. In some embodiments, step 712 may include removing the cutting rib from the cutting rib assembly, to perform at least one of cleaning the cutting rib, re-tooling the cutting rib, or replacing the cutting rib. In some embodiments, step 712 may include detaching the cutting rib from the centralizer to remove portions of tissue (e.g., bone tissue, cartilage, and the like) from the cutting rib, the centralizer, or both, and grafting the removed portions of tissue back into the bone or other patient's tissue. In some embodiments, step 712 may further include collecting and storing the removed portions of tissue for biopsy analysis, or disposal. In some embodiments, step 712 may further include forming a shape in a bone for receiving an implant by cutting bone with the cutting rib assembly.

While the above description contains many specifics, these should not be construed as limitations on the scope of the disclosure, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims when filed.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of X, Y, and Z" or "at least one of X, Y, or Z" each refer to only X, only Y, or only Z; any combination of X, Y, and Z; and/or at least one of each of X, Y, and Z.

Embodiments disclosed herein include, at least, the following:

A. A device including a cutting rib, the cutting rib including an arcuate portion having an outer sharp edge and a centralizer configured to receive the cutting rib through a radial slot, the radial slot forming a gap with the cutting rib. The arcuate portion of the cutting rib is formed into a profile that follows a surface of the centralizer, the outer sharp edge of the arcuate portion of the cutting rib has a wavy profile that forms a tunnel in the gap between the centralizer and the cutting rib, and the outer sharp edge of the arcuate portion of the cutting rib protrudes outwardly from the surface of the centralizer.

B. A method includes joining a cutting rib and a centralizer to form a cutting assembly, and joining the cutting assembly to a reamer handle. The method also includes providing a rotating motion to the cutting rib assembly through the reamer handle, removing a substrate material by contacting the cutting assembly with a substrate, and adjusting the rotating motion of the cutting rib assembly through the reamer handle according to a substrate condition.

Each of embodiments A, and B, may have one or more of the following additional elements in any combination. Element 1, wherein the centralizer is concentric with the outer sharp edge of the arcuate portion of the cutting rib, thereby centering a cutting action at a center point of the centralizer. Element 2, wherein the centralizer is not concentric with the outer sharp edge of the arcuate portion of the cutting rib, thereby centering a cutting action off a center point of the centralizer. Element 3, wherein the centralizer receives the cutting rib through the radial slot so that a distal portion of the centralizer reaches farther than a center point of the outer sharp edge of the arcuate portion. Element 4, further including multiple cutting ribs assembled symmetrically about an axis of rotation of the device, wherein the centralizer includes one radial slot for each of the multiple cutting ribs. Element 5, wherein the centralizer has a hemi-spherical shape to cut into a substrate shaped at least partially in a spherical portion. Element 6, wherein the centralizer has a shape configured to form a cutout portion consistent with the acetabular region of a patient's hip. Element 7, wherein at least one of the centralizer or the cutting rib is disposable after one or more uses. Element 8, further including a crossbar at a proximal end of the cutting rib, wherein the crossbar is configured to couple with a reamer handle configured to provide a rotating motion about a symmetry axis of the centralizer. Element 9, further including a geometry at a proximal end of the cutting rib, wherein the geometry is configured to couple with a reamer handle configured to provide a rotating motion about a symmetry axis of the centralizer. Element 10, wherein the centralizer includes a plurality of portions assembled together on the cutting rib. Element 11, wherein the radial slot includes an open rail having a wider gap between the centralizer and the cutting rib, to allow substrate material cut by the cutting rib to an interior side of the centralizer. Element 12, wherein the radial slot forms a first gap with the cutting rib at a proximal region on a back end of the cutting rib relative to a cutting direction, and a second and a third gaps with the cutting rib at a distal region on a front end of the cutting rib relative to the cutting direction, wherein the first gap is different in size than the second gap, the second gap is smaller than the third gap, and the third gap is approximately two millimeters or more. Element 13, wherein the radial slot forms a first gap with the cutting rib at a proximal region on a back end of the cutting rib relative to a cutting direction, and a second and a third gaps with the cutting rib at a distal region on a front end of the cutting rib relative to the cutting direction, wherein the first gap is less than half a millimeter, the second gap is about one millimeter, and the third gap is greater than two millimeters. Element 14, wherein the centralizer is configured to collect and store a portion of the substrate material that is cut away by the cutting rib in an interior side of the centralizer. Element 15, wherein the gap formed between the radial slot and the cutting rib is uniform in a back side of the cutting rib and increases in size along a distal direction on a front side of the cutting rib. Element 16, wherein the centralizer is configured to be mechanically decoupled from the cutting rib. Element 17, further including a second cutting rib, wherein the centralizer receives the second cutting rib through a second radial slot forming a second gap with the second cutting rib, and wherein the gap and the second gap are configured to reduce a torque transmitted from the cutting rib to the second cutting rib. Element 18, further including a central portion comprising the cutting rib and at least a second cutting rib, and a central core providing support to the cutting rib and the at least second cutting rib, wherein the second cutting rib could transmit torque to the cutting rib through the central core. Element 19, wherein the crossbar is configured to be mechanically coupled to a reamer handle, the reamer handle configured to provide a rotating motion to the cutting rib, and the cutting rib providing the rotating motion to the centralizer.

Element 20, further including forming a shape in a bone for receiving an implant by cutting bone with the cutting rib assembly. Element 21, further including selectively replacing a portion of the cutting rib assembly according to a cutting rib assembly condition. Element 22, further including measuring a temperature of the substrate and reducing a rotating speed when the temperature exceeds a pre-selected threshold. Element 23, wherein adjusting the rotating motion of the cutting rib assembly includes adjusting an orientation of the reamer handle relative to the substrate to cut a selected shape in the substrate. Element 24, wherein adjusting the rotating motion of the cutting rib assembly includes stopping the rotating motion to separate the centralizer from the cutting rib and replacing at least one of the centralizer or the cutting rib. Element 25, wherein adjusting the rotating motion of the cutting rib assembly includes increasing a rotating speed when the cutting rib assembly reaches a harder portion of the substrate.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A device, comprising:
   a cutting rib, the cutting rib including an arcuate portion having an outer sharp edge; and
   a centralizer configured to receive the cutting rib through a radial slot, the radial slot forming a gap with the cutting rib, wherein:
   the arcuate portion of the cutting rib is formed into a profile that follows a surface of the centralizer,
   the outer sharp edge of the arcuate portion of the cutting rib has a wavy profile having angulated edges and alternating planar cutting surfaces that follow the surface of the centralizer and form a wavy radial rib including at least one tunnel in the gap between the centralizer and the cutting rib, and
   the outer sharp edge of the arcuate portion of the cutting rib protrudes outwardly from the surface of the centralizer.

2. The device of claim 1, wherein the centralizer is concentric with the outer sharp edge of the arcuate portion of the cutting rib, thereby centering a cutting action at a center point of the centralizer.

3. The device of claim 1, wherein the centralizer is not concentric with the outer sharp edge of the arcuate portion of the cutting rib, thereby centering a cutting action off a center point of the centralizer.

4. The device of claim 1, wherein the centralizer receives the cutting rib through the radial slot so that a distal portion of the centralizer reaches farther than a center point of the outer sharp edge of the arcuate portion.

5. The device of claim 1, further comprising multiple cutting ribs assembled symmetrically about an axis of rotation of the device, wherein the centralizer comprises one radial slot for each of the multiple cutting ribs.

6. The device of claim 1, wherein the centralizer has a hemi-spherical shape to cut into a substrate shaped at least partially in a spherical portion.

7. The device of claim 1, wherein the centralizer has a shape configured to form a cutout portion consistent with an acetabular region of a patient's hip.

8. The device of claim 1, wherein at least one of the centralizer or the cutting rib is disposable after one or more uses.

9. The device of claim 1, further comprising a crossbar at a proximal end of the cutting rib, wherein the crossbar is configured to couple with a reamer handle configured to provide a rotating motion about a symmetry axis of the centralizer.

10. The device of claim 1, further comprising a geometry at a proximal end of the cutting rib, wherein the geometry is configured to couple with a reamer handle configured to provide a rotating motion about a symmetry axis of the centralizer.

11. The device of claim 1, wherein the radial slot comprises an open rail having a wider gap between the centralizer and the cutting rib, to allow substrate material cut by the cutting rib to an interior side of the centralizer.

12. The device of claim 1, wherein the centralizer is configured to collect and store a portion of a substrate material that is cut away by the cutting rib in an interior side of the centralizer.

13. The device of claim 1, wherein the centralizer is configured to be mechanically decoupled from the cutting rib.

14. The device of claim 1, further comprising a second cutting rib, wherein the centralizer receives the second cutting rib through a second radial slot forming a second gap with the second cutting rib, and wherein the gap and the second gap are configured to reduce a torque transmitted from the cutting rib to the second cutting rib.

15. The device of claim 1, further comprising a central portion comprising the cutting rib and at least a second cutting rib, and a central core providing support to the cutting rib and the at least second cutting rib, wherein the second cutting rib could transmit torque to the cutting rib through the central core.

16. The device of claim 1, further including a crossbar configured to be mechanically coupled to a reamer handle, the reamer handle configured to provide a rotating motion to the cutting rib, and the cutting rib providing the rotating motion to the centralizer.

* * * * *